United States Patent
Andersen et al.

(10) Patent No.: US 6,833,376 B2
(45) Date of Patent: Dec. 21, 2004

(54) 5-AMINOALKYL AND 5-AMINOCARBONYL SUBSTITUTED INDOLES

(75) Inventors: Kim Andersen, Virum (DK); Jens Kristian Perregaard, Jægerspris (DK); Thomas Balle, København S (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 0 days.

(21) Appl. No.: 10/097,126

(22) Filed: Mar. 8, 2002

(65) Prior Publication Data

US 2002/0169169 A1 Nov. 14, 2002

Related U.S. Application Data

(63) Continuation of application No. PCT/DK00/00496, filed on Sep. 8, 2000.
(60) Provisional application No. 60/153,460, filed on Sep. 9, 1999.

(30) Foreign Application Priority Data

Sep. 9, 1999 (DK) ........................ 1999 01273

(51) Int. Cl.$^7$ ..................... A61K 31/445; C07D 401/14
(52) U.S. Cl. ........................ 514/323; 546/201
(58) Field of Search ..................... 514/323; 546/201

(56) References Cited

U.S. PATENT DOCUMENTS

| | | | | |
|---|---|---|---|---|
| 5,521,196 A | * | 5/1996 | Audia et al. ............... | 514/323 |
| 5,703,087 A | | 12/1997 | Perregaard et al. ......... | 514/278 |
| 5,721,252 A | * | 2/1998 | Audia ......................... | 514/323 |

FOREIGN PATENT DOCUMENTS

| | | | | |
|---|---|---|---|---|
| WO | 92/15301 | | 9/1992 | ......... A61K/31/445 |
| WO | WO 97/27186 | * | 7/1997 | |
| WO | 99/46259 | | 9/1999 | ......... C07D/401/14 |

* cited by examiner

Primary Examiner—Celia Chang
(74) Attorney, Agent, or Firm—Darby & Darby

(57) ABSTRACT

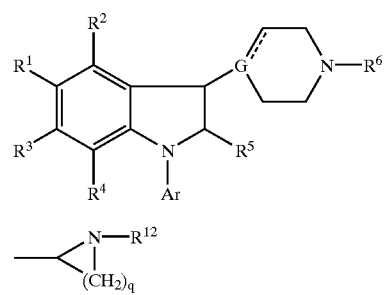

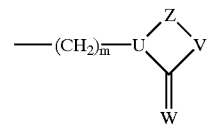

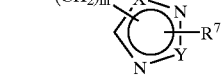

The present invention relates to 5-aminoalkyl and 5-aminocarbonyl substituted indole derivatives having formula (1), wherein $R^1$ is -$(CH_2)_{n-1}$-$CONR^{10}R^{11}$, -$(CH_2)_n$-$CONR^{10}R^{11}$ or (a), wherein $R^{10}$ and $R^{11}$ independently are selected from substituents defined herein; n is 1 to 3 and q is 2 to 5; G is N, C, or CH; Ar is phenyl optionally substituted with one or more substituents, or Ar is heterocyclic; $R^2$, $R^3$, $R^4$, $R^5$ and $R^6$ are independently selected from substituents defined herein; m is an integer from 2–6; W is O or S; U is N or CH; Z is —$(CH_2)_p$-, p being 2 or 3, or Z is —CH=CH— or 1,2-phenylene, or Z is —$COCH_2$- or —$CSCH_2$-; V is O, S, $CH_2$, or $NR^9$; X is N, C, or CH; Y is N, C, or CH; provided at least one of X and Y is N; or a pharmaceutically acceptable acid addition salt thereof. The novel 5-substituted indoles have high affinity for $\alpha_1$-adrenoceptors and are considered useful for the treatment of diseases or disorders responsive to $\alpha_1$-adrenoceptor antagonists. Further, as the compounds are selective $\alpha_1$-adrenoceptor ligands they may be particularly useful as PET or SPECT ligands.

9 Claims, No Drawings

5-AMINOALKYL AND 5-AMINOCARBONYL SUBSTITUTED INDOLES

This application claims priority under 35 U.S.C. §119(e) of provisional application Ser. No. 60/153,460, filed Sep. 9, 1999, and is a continuation of International application Ser. No. PCT/DK00/00496, filed Sep. 8, 2000. The disclosure of both priority applications is hereby incorporated by reference.

The present invention relates to novel 5-aminoalkyl and 5-aminocarbonyl substituted indoles having high affinity for $\alpha_1$-adrenoceptors. The compounds of the invention are considered useful for the treatment of diseases or disorders responsive to antagonism of the $\alpha_1$-adrenoceptor. Further, as the compounds are selective $\alpha_1$-adrenoceptor ligands they may be particularly useful as PET or SPECT ligands.

BACKGROUND

U.S. Pat. No. 4.710.500 discloses 5-substituted indole derivatives having the general formula:

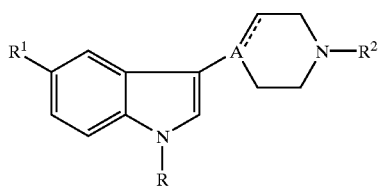

The compounds may be substituted in position 5 with a substituent selected from halogen, lower alkyl, lower alkoxy, hydroxy, cyano, nitro, lower alkylthio, $CF_3$, lower alkylsulphonyl, amino, lower alkylamino and lower di-alkylamino. The compounds are claimed to be potent and long-lasting dopamine antagonists, and accordingly useful for the treatment of psychoses. The compounds are also claimed to be strong 5-HT antagonists indicating effects in the treatment of negative symptoms of schizophrenia and depression and for the treatment of cardiovascular diseases.

The use of sertindole having the formula

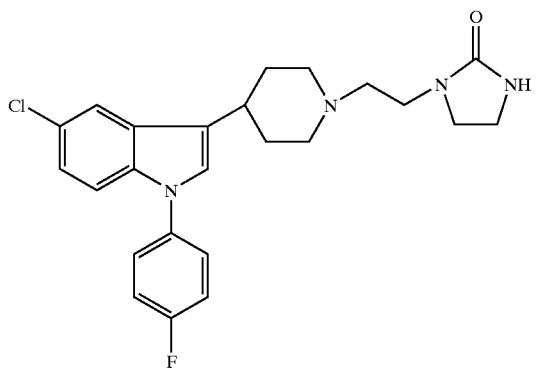

as an antipsychotic is specifically claimed in EP-A2-0 392 959.

This type of compounds has also been shown to be useful for the treatment of a range of other disorders including anxiety (WO 92/00070), cognitive disorders (WO 92/15303), abuse (WO 92/15302) and hypertension (WO 92/15301).

WO 92/15301 discloses compounds having affinity for the $\alpha_1$-adrenoceptor. However, the compounds disclosed therein are not selective for the $\alpha_1$-adrenoceptor.

Interest in the development of $\alpha_1$-adrenoceptor antagonists has primarily focused on therapeutics for the treatment of cardiovascular diseases (Hieble et al., *Exp. Opin. Invest. Drugs*, 1997, 6, 3657). Prazosin is the prototype of an $\alpha_1$-adrenoceptor antagonist which has very potent peripheral effects. Prazosin is considered to have poor CNS penetration although it in some animal models have shown effects indicating potency in the central nervous system. Until now, no $\alpha_1$-adrenoceptor selective antagonists with good CNS penetration to the human brain have been available.

Evidence exists indicating that blockade of $\alpha_1$-adrenoceptor neurotranstission could be beneficial i the treatment of schizophrenia. Most classical antipsychotics including clozapine b potently to a,-adrenoceptors labelled with [$^3$H]prazosin or [$^3$H]WB-4101. Some studies seem to indicate a central role of the $\alpha_1$-component for the atypical profile of clozapine. ( Baldessarini, et al., *Br. J. Psychiatry*, 1992, 160, 12–16 and Prinssen, et al., *Eur. J. PharmacoL*, 1994, 262, 167–170). Further, repeated co-administration of prazosin and haloperidol was found to reduce the effect of haloperidol on the firing of dopamine neurons in nigrostriatal areas, suggesting that the combination would be effective as antipsychotic treatment without producing extrapyramidal side effects (EPS) (Chiodo, et al., *J Neurosci.* 1985, 3, 2539–2544).

It has also been suggested that centrally acting $\alpha_1$-adrenoceptor antagonists will have antimanic effects while corresponding agonists would be beneficial for the treatment of depression (Lipinsky, et al., *Life Sciences*, 1987, 40, 1947–1963).

Labelled compounds of the present invention are considered to be valuable PET (positron emission tomography) ligands and SPECT (single photon emission computed tomography) ligands due to their selectivity for $\alpha_1$-adrenoceptors.

Finally, it is well established that $\alpha_1$-adrenoceptor antagonists acting peripherally are useful for the treatment of benign prostatic hyperplacia, hypertension and cardiac arrhyttnias and for the reduction of intra ocular pressure.

THE INVENTION

Accordingly, the present invention relates to 5-aminoalkyl and 5-aminocarbonyl substituted indole derivatives having the general formula:

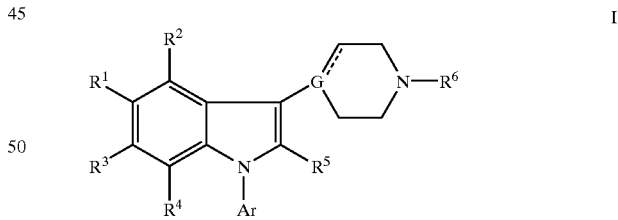

I wherein
$R^1$ is $-(CH_2)_{n-1}-CONR^{10}R^{11}$, $-(CH_2)_n-NR^{10}R^{11}$ or

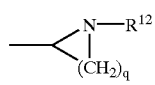

wherein $R^{10}$ and $R^{11}$ independently are selected from hydrogen, $C_{1-6}$-alkyl, $C_{2-6}$-alkenyl, $C_{2-6}$-alkynyl $C_{3-8}$-cycloalkyl, $C_{3-8}$-cycloalkyl-$C_{1-6}$-alkyl, aryl-$C_{1-6}$-alkyl, aryl, acyl, amino-$C_{1-6}$-alkyl and mono- or di-$C_{1-6}$-alkylamino-$C_{1-6}$-alkyl, $R^{12}$ is hydrogen or $C_{1-6}$-alkyl, n is 1 to 3 and q is 2 to 5;

G is N, C, or CH; the dotted line meaning a bond when G is C, and the dotted line meaning no bond when G is CH, or N;

Ar is phenyl optionally substituted with one or more substituents independently selected from halogen, $C_{1-6}$-alkyl, $C_{1-6}$-alkoxy, hydroxy, trifluoromethyl and cyano, or Ar is 2-thienyl, 3-thienyl, 2-furanyl, 3-furanyl, 2-thiazolyl, 2-oxazolyl, 2-imidazolyl, 2-pyridyl, 3-pyridyl, or 4-pyridyl;

$R^2$, $R^3$, $R^4$ and $R^5$ are independently selected from hydrogen, $C_{1-6}$-alkyl, $C_{1-6}$-alkoxy, hydroxy, halogen, trifluoromethyl, nitro, cyano, amino, $C_{1-6}$-alkylamino and $C_{1-6}$-dialkylamino;

$R^6$ is hydrogen, or $C_{3-8}$-cycloalkyl, $C_{3-8}$-cycloalkyl-$C_{1-6}$-alkyl, $C_{1-6}$-alkyl, $C_{2-6}$-alkenyl or $C_{2-6}$-alkenyl, which may optionally be substituted with one or two hydroxy groups, any hydroxy group present being optionally esterified with an aliphatic carboxylic acid having from two to twentyfour carbon atoms inclusive, or $R^6$ is a group of the Formula II or III:

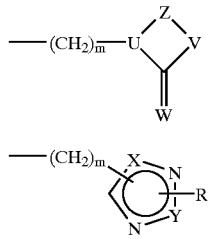

II

III wherein m is an integer from 2–6;
W is O, or S;
U is N or CH;
Z is —$(CH_2)_p$-, p being 2 or 3, or Z is —CH=CH— or 1,2-phenylene optionally substituted with halogen or trifluoromethyl, or Z is —$COCH_2$- or —$CSCH_2$-;
V is O, S, $CH_2$, or $NR^9$, wherein $R^9$ is hydrogen, or $C_{1-6}$-alkyl, $C_{2-6}$-alkenyl or $C_{2-6}$-alkenyl which may optionally be substituted with one or two hydroxy groups, or a $C_{3-8}$-cycloalkyl or $C_{3-8}$-cycloalkyl-$C_{1-6}$-alkyl group;
X is N, C, or CH; Y is N, C, or CH; provided at least one of X and Y is N; and $R^7$ is hydrogen, or $C_{1-6}$-alkyl;
or a pharmaceutically acceptable acid addition salt thereof In a particular embodiment, the present invention relates to compounds wherein $R^1$ is —$CONR^{10}$ $^{R11}$ or —$(CH_2)_n$-$NR^{10}R^{11}$ wherein $R^{10}$ and $R^{11}$ are independently selected from hydrogen, $C_{1-6}$alkyl and acyl.

In another particular embodiment, $R^6$ is a group of formula II, in particular a 2-imidazolidinon ring.

Such compounds include in particular the compounds:

1-(4-Fluorophenyl)-3-[1-[2-(2-imidazolidinon-1-yl)ethyl]-4-piperidinyl]-N-methyl-1H-indole-5-carboxamide;

N,N-Dimethyl-1-(4fluorophenyl)-3-[1-[2-(2-imidazolidinon-1-yl)ethyl]-4-piperidinyl]-1H-indole-5-carboxamide;

1-[2[4-[5-Dimethylaminomethyl-1-(4-fluorophenyl)-1H-indol-3-yl]-1-piperidinyl ]ethyl]2-imidazolidinon;

1-[2[4[5-Dimethylaminomethyl-1-(4-fluorophenyl)-1H-indol-3-yl]-1,2,3,6-tetrahydropyridin-1-yl]ethyl]-2-imidazolidinon;

1-[2[4-[1-(4fluorophenyl)-5-methylaminomethyl-1H-indol-3-yl]-1-piperidinyl]ethyl ]-2-imidazolidinon; or 1-[2[4-[5-aminomethyl-1-(4fluorophenyl)-1H-indol-3-yl]-1-piperidinyl]ethyl ]-2-irnidazolidinon;

or a pharmaceutically acceptable acid addition salt thereof.

The present invention also relates to a pharmaceutical composition comprising at least one compound as above or a pharmaceutically acceptable acid addition salt thereof and optionally a second pharmaceutically active ingredient in combination with one or more pharmaceutically acceptable carrier or diluents.

The present application relates to the use of a compound as above and optionally a second pharmaceutically active ingredient for the preparation of a medicament for the treatment of a disorder or disease responsive to antagonism of $\alpha_1$-adrenoceptors.

The present invention also relates to a method for the treatment of a disorder or disease responsive to antagonism of $\alpha_1$-adrenoceptors in a mammal comprising administering a compound as above or an acid addition salt thereof and optionally a second pharmaceutically active ingredient to said mammal.

In a particular embodiment, the second pharmaceutically active ingredient is an agent having antipsychotic activity.

In still another embodiment, the present invention relates to the use of a compound as above or an acid addition salt thereof for the preparation of a radio-labelled compound of the Formula I.

Diseases or disorders responsive to antagonism of $\alpha_1$-adrenoceptors includes psychosis, mania, benign prostatic hyperplacia, hypertension, cardiac arrhytmias and reduction of intra ocular pressure.

In a further embodiment, the present invention relates to a compound of formula I which is radio-labelled, e.g. with [$^{11}$C]-methyl.

Finally, the present invention relates to the use of radio-labelled compounds of formula I in various biological assays, including binding assays, and in PET- or SPECT studies.

DETAILED DESCRIPTION OF THE INVENTION

When used herein halogen means fluoro, chloro, bromo or iodo.

The term $C_{1-6}$ alkyl refers to a branched or unbranched alkyl group having from one to six carbon atoms inclusive, including groups such as methyl, ethyl, 1-propyl, 2-propyl, 1-butyl, 2-butyl, 2-methyl-2-propyl and 2-methyl-1-propyl. Similarly, $C_{2-6}$-alkenyl designates such groups having from two to six carbon atoms, containing one double bond, including groups such as ethenyl, propenyl and butenyl and $C_{2-6}$ alkenyl designates groups having from two to six carbon atoms and containing one triple bond, including groups such as ethynyl, propynyl.

The term acyl refer to $C_{1-6}$-alkylcarbonyl, arylcarbonyl and aryl-$C_{1-6}$alkylcarbonyl.

The terms $C_{1-1}$-alkoxy, $C_{1-6}$-alkylaimino, $C_{1-6}$-dialkylamino, $C_{1-6}$-alkylcarbonyl, aryl-$C_{1-6}$ alkylcarbonyl etc. designate such groups in which $C_{1-6}$-alkyl is as defined above.

The term $C_{3-8}$-g-cycloalkyl designates a monocyclic or bicyclic carbocycle having three to eight C-atoms including such groups as cyclopropyl, cyclopentyl, cyclohexyl, etc.

The acid addition salts of the compounds of the invention are pharmaceutically acceptable salts formed with non-toxic acids. Exemplary of such organic salts are those with maleic, fumaric, benzoic, ascorbic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzenesulfonic, and theophylline acetic acids, as well as the 8-halotheophyllines, for example 8-bromotheophylline. Exemplary of such inorganic salts are those with hydrochloric, hydrobromic, sulfuric, sulfamic, phosphoric, and nitric acids.

The selectivity of the compounds of the invention for the $\alpha_1$-adrenoceptor makes them particularly useful for the development of labelled ligands useful in various biological assays and in PET and SPECT studies.

The compounds of the invention can be labelled by the use of radio-labelled precursors, including $^{11}$C-labelled precursors such as [$^{11}$C]methyl iodide, [$^{11}$C]methyl triflate, etc. The compounds may also be labelled with $^{18}$F or $^{123}$I.

The compounds of the present invention can be prepared according to the procedures described below:

a) Reacting an indole derivative of the following formula

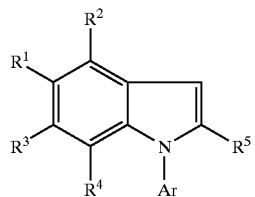

IV wherein $R^1$, $R^2$, $R^3$, $R^4$, $R^5$ and Ar, are as defined above, with a 4-piperidone of the formula

wherein $R^6$ is as defined above A is an oxo group, or a —O—(CH$_2$)$_s$—O—chain, wherein s is 2, or 3;

b) reducing the tetrahydropyridine double bond in a compound of the formula

VI

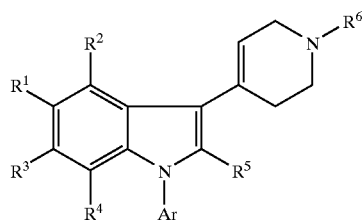

wherein $R^1$, $R^2$, $R^3$, $R^4$, $R^5$, $R^6$ and Ar, are as defined above;

c) reacting a compound of the formula

VII

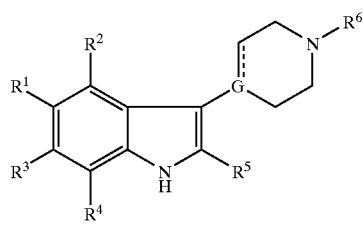

wherein $R^1$, $R^2$, $R^3$, $R^4$, $R^5$, $R^6$, G, and the dotted line, are as defined above, with a compound of the formula Ar-Hal wherein Ar is as defined above and "Hal" is halogen, in the presence of a metal catalyst, d) reacting a compound of the formula

VIII

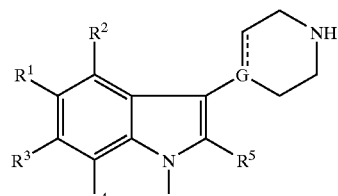

wherein $R^1$, $R^2$, $R^3$, $R^4$, $R^5$, G, the dotted line and Ar, are as defined above, with a reagent of formula $R^0$-L wherein $R^0$ is $C_{3-8}$-cycloalkyl, $C_{3-8}$-cycloalkyl-$C_{1-6}$-alkyl, $C_{1-6}$-alkyl, or $C_{2-6}$-alkenyl and L is halogen, mesylate, or tosylate, or an epoxide of formula

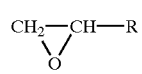

wherein R is hydrogen, or $C_{1-4}$-alkyl;

e) reducing the carbonyl group of a compound of the formula

IX

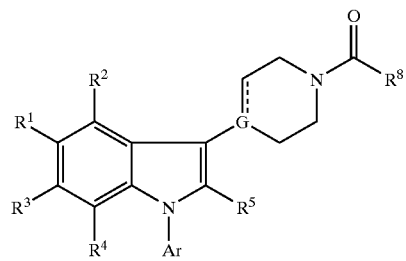

wherein $R^1$, $R^2$, $R^3$, $R^4$, $R^5$, G, the dotted line and Ar, are as defined above and $R^8$ is $C_{3-8}$-cycloalkyl, $C_{1-5}$-alkyl, $C_{3-8}$-cycloalkyl-$C_{1-5}$-alkyl;

f) decarboxylating a compound of the formula

X

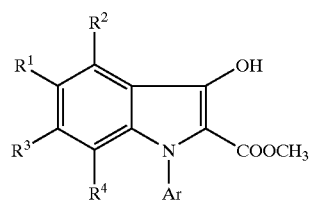

wherein $R^1$, $R^2$, $R^3$, $R^4$ and Ar, are as defined above, followed by reaction with a piperazine of the formula

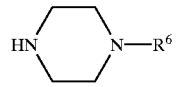

wherein $R^6$ is as defined above;

g) reacting a compound having the formula

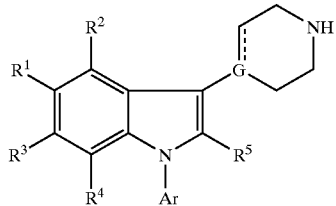

XII wherein $R^1$, $R^2$, $R^3$, $R^4$, $R^5$, G, the dotted line and Ar, are as defined above with a compound having the formula Hal-$R^x$ wherein $R^x$ is a group of formula II or III as defined above and "Hal" is chloro, bromo, or iodo;

h) reducing a compound of the formula

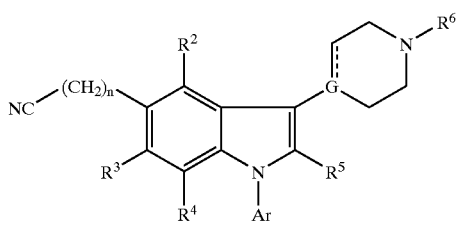

XIII wherein $R^2$, $R^3$, $R^4$, $R^5$, $R^6$, G, the dotted line, Ar and n are as defined above;

i) reducing a compound of the formula

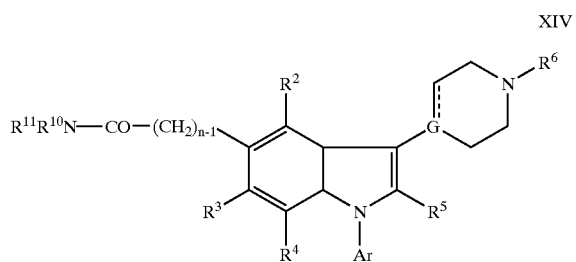

XIV wherein $R^2$, $R^3$, $R^4$, $R^5$, $R^6$, $R^{10}$, $R^{11}$, G, the dotted line, Ar and n are as defined above;

j) coupling a compound of formula

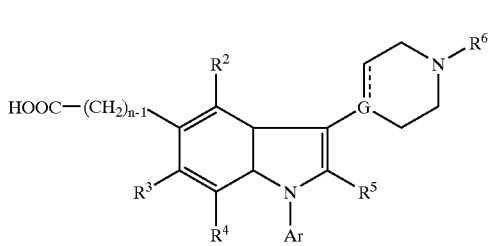

XV wherein $R^2$, $R^3$, $R^4$, $R^5$, $R^6$, G, the dotted line n and Ar are as defined above with an amine of formula $HNR^{10}R^{11}$ wherein $R^{10}$ and $R^{11}$ are as defined above;

k) reacting a compound of formula

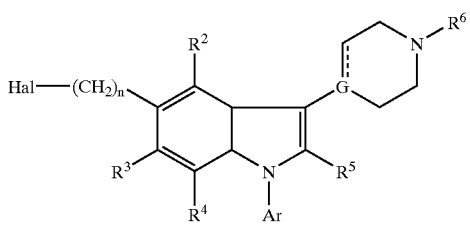

XVI wherein $R^2$, $R^3$, $R^4$, $R^5$, $R^6$, G, the dotted line "Hal", n and Ar are as defined above with an amine of formula $HNR^{10}R^{11}$ wherein $R^{10}$ and $R^{11}$ are as defined above; or l) reacting a compound of formula

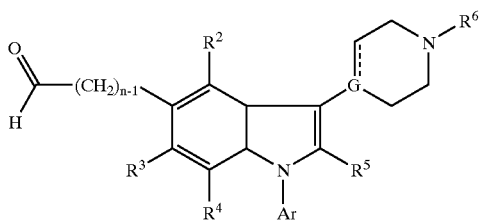

XVII wherein $R^2$, $R^3$, $R^4$, $R^5$, $R^6$, G, the dotted line, n and Ar are as defined above with an amine of formula $HNR^{10}R^{11}$ wherein $R^{10}$ and $R^{11}$ are as defined above, using reductive conditions.

Methods for the preparation of the starting materials used in the above processes are described in U.S. Pat. No. 4.710.500, WO 92/00070, PCT/DK99/00119 and in Perregaard et al., *J.Med.Chem.*, 1992 (35), 1092–1101, or can be prepared analogously to the procedures described herein.

The 5-cyanomethyl-indoles may be prepared from the corresponding 5-yano-indoles. The 5-cyano-indoles are hydrolysed to form the corresponding carboxylic acid which are subsequently reduced to the corresponding alcohols. Reaction with methanesulphonyl chloride to form the corresponding 5-chloromethyl-indoles followed by reaction with a cyanide afford the 5-cyanomethyl-indoles. Accordingly, homologous compounds may be prepared in a sequential manner.

The carboxainides of formula XIV, carboxylic acid derivatives of formula XV, the alkylhalogenides of formula XVI and the aldehydes of formula XVII were prepared from the corresponding nitrites by methods obvious to the chemist skilled in the art.

In method a) the reaction is performed under strong acidic conditions by heating. Trifluoroacetic acid or HCl in ethanol are preferred as acidic catalysts.

In method b) and h) the reduction is preferably carried out at low hydrogen pressures (3 Ato.) in the presence of platinum or palladium on carbon black.

In method c) the arylation is preferably carried out at about 160–210° C. in aprotic polar solvents as e.g. 1-methyl-2-pyrrolodinone or hexamethylphosphoric triamide with $K_2CO_3$ as base and copper as a catalyst.

In method e) the reduction is preferably carried out with $LiALH_4$ in 1THF or diethylether or with diborane in THF.

Method f) is a two step procedure in which compound X is first decarboxylated in the presence of an inorganic salt as e.g. LiCl or $MgCl_2$ in a polar solvent as e.g. diglyme, hexamethylphosphoric triamide or 1-methyl-2-pyrrolidone at elevated temperatures (120–150° C.). Finally, the appropriate piperazine is added and the temperature raised to about 200° C. and kept there until the corresponding indoxyle has disappeared according to TCL analysis. The compounds of Formula X are conveniently prepared according to the procedures reported by P. C. Unangst and M. E. Carethers, J. Heterocyclic Chem., 21, 709 (1984).

The alkylations in method d), g) and k) are preferably performed as outlined in U.S. Pat. No. 4.710.500, WO 92/00070 and in Perregaard et al., J.Med.Chem., 1992 (35), 1092–1101

The amide in method i) is preferably reduced by means of standard conditions using $Al_3$, $LiAlH_4$ or borane in an aprotic solvent such as diethyl ether or tetrahydrofiuran The coupling reaction in step j) is preferably performed by formation of the active ester, the mixed anhydride, or the intermediate acid chloride and subsequent reaction with the amine. The reductive amination reaction in method 1) is performed preferably by $NaCNBH_4$ in a protic solvent such as methanol.

In the following, the invention is further illustrated by way of examples which, however, may not be construed as limiting.

Experimental Section

All reactions were carried out under a positive pressure of nitrogen. Melting points were determined on a Büchi SMP-20 apparatus and are uncorrected. Mass spectra were obtained on a Quattro MS-MS system from VG Biotech, Fisons Instruments. The MS-MS system was connected to an HP 1050 modular HPLC system. A volume of 20–50 $\mu l$ of the sample (10 $\mu g/mL$) dissolved in a mixture of 1% acetic acid in acetonitril/water 1:1 was introduced via the autosampler at a flow of 30 $\mu l/min$ into the Electrospray Source. Spectra were obtained at two standard sets of operating conditions. One set to obtain molecular weight information (MH+) (21 eV) and the other set to induce fragmentation patterns (70 eV). The background was subtracted. The relative intensities of the ions are obtained from the fragmentation pattern. When no intensity is indicated for the Molecular Ion (MH+), this ion was only present under the first set of operating conditions. 1H NMR spectra were recorded of all novel compounds at 250 MHz on a Bruker AC 250 or at 500 MHz on a Bruker Avance DRX500 instrument. Deuterated chloroform (99.8%D) or dimethyl sulfoxide (99.9%D) were used as solvents. TMS was used as internal reference standard. Chemical shift values are expressed in ppm-values. The following abbreviations are used for multiplicity of NMR signals: s=singlet, d=doublet, t=triplet, q=quartet, qui=quintet, h=heptet, dd=double doublet, dt=double triplet, dq=double quartet, tt=triplet of triplets, m=multiplet. NMR signals corresponding to acidic protons are generally omitted. Content of water in crystalline compounds was determined by Karl Fischer titration. Standard workup procedures refer to extraction with the indicated organic solvent from proper aqueous solutions, drying of combined organic extracts (anhydrous $MgSO_4$ or $Na_2SO_4$), filtering and evaporation of the solvent in vacuo. For column chromatography, silica gel of type Kieselgel 60,230–400 mesh ASTM was used.

EXAMPLE 1

1-(4-Fluorophenyl)-1H-indole-5-carboxylic acid (1)
5-Cyano-1-(4-fluorophenyl)-1H-indole (60 g) and potassium hydroxide (60 g) was refluxed for 24 h in 90% ethanol. Water (1.5 L) was added and the aqueous phase extracted twice with isopropyl ether. After acidifying with hydrochloric acid, the title compound was filtered off and dried. Mp. 224–227° C. $^1$H-NMR (DMSO):6.9 (d, IH), 7.45 (t, 2H), 7.55 (d, 1H), 7.6–7.72 (m, 3H), 7.85 (d, 1H), 8.4 (s, 1H) 12.9–12.5 (1H, s, broad).

EXAMPLE 2

N,N-Dimethyl-1-(4fluorophenyl)-1H-indole-5-carboxamide (2) 1-(4-Fluorophenyl)-1H-indole-5-carboxylic acid (20 g) and triethyl amine (8 g) in methylene chloride was cooled to −30° C. Ethyl chloroformate (8.7 g) was added and the temperature kept below −10° C. for 2 h. Dimethyl amine (16 g, 33% in ethanol) was added at −10° C. After addition, the cooling bath was removed and the solution was stirred at room temperature. Water and NaOH was added and the mixture was extracted with methylene chloride after evaporation of the solvent the title compound was filtered through silica gel using ethylacetate/heptane 20:80 and the solvent removed in vacuo. Yield: 12 g (oil). $^1$H-NMR ($CDCl_3$) 3.10 (s, 6H), 6.70 (s, 1H), 7.20 (t, 2H), 7.20–7.35 (m, 2H) (m, 3H), 7.80 (s, 1H)

EXAMPLE 3

1-(4-Fluorophenyl)-N-methyl-1H-indole-5-carboxamide (3) 1-(4-Fluorophenyl)-1H-indole-5-carboxylic acid (16 g) was dissolved in THF (120 mL). 1,1'-Carbonyldiimidazole (15 g) was added and the solution was stirred at room temperature for 50 minutes. After cooling to 0° C., methyl amine (125 mL, 2M in TBF) was added keeping the solution below 10° C. After addition, the solution was stirred for 20 minutes at 0° C. and 45 minutes at room temperature. After removal of the solvent, the reaction mixture was dissolved in ethyl acetate, washed with water, saturated aqueous $NaHCO_3$ and dried over $MgSO_4$. The product was recrystalised from ethyl acetate/heptane 1:3. Yield: 12.3 g. Mp. 126–128° C. Analysis: Calc: C: 71.63, H: 4.88, N: 10.44; Found C: 71.38, H: 5.05, N: 10.72 $^1$H-NMR (DMSO): 2.80 (d, 3H), 6.80 (d, 1H), 7.45 (t, 2H), 7.50 (d, 1H), 7.65 (m, 2H) (m, 2H), 8.20 (s, 1H), 8.40 (d, broad, 1H)

EXAMPLE 4

1-(4-Fluorophenyl)-N-methyl-3-(1,2,3,6-tetrahydro-4-pyridyl)-1H-indole-5-carboxamide (4a)

A solution of 1-(4-Fluorophenyl)-N-methyl-1H-indole-5-carboxamide (3) (12.3 g) in a mixture of acetic acid (60 mL) and trifluoroacetic acid (15 rnL) was added during 0.5 h to a refluxing solution of 4-piperidon, HCl, $H_2O$ (36.6 g) in a mixture of acetic acid (50 mL) and trifluoroacetic acid (100 mL). The reaction mixture was refluxed for 1h, cooled to room temperature and the solvents were removed in vacuo. Water was added and pH was adjusted to 10 by addition of aqueous NaOH. The aqueous phase was extracted with ethyl acetate. The combined organic phases were washed with water and brine and dried over $MgSO_4$. Evaporation of the solvents in vacuo afforded the title compound as a foam.Yield 16 g. $^1$H-NMR (DMSO) 2.48 (s, broad, 2H), 2.80 (d. 3H), 2.98 (t, 2H), 3.50 (d, 2H), 6.40(s, 1H) 7.45 (t, 2H), 7.50 (d, 1H), 7.65 (dd, 2H), 7.70–7.80 (m, 2H), 8.40 (s, 1H), 8.45 (q, broad, 1H)

The following compound was prepared accordingly:
N,N-Dimethyl-1(4-fluorophenyl)-3-(1,2,3,6-tetrahydro-4-pyridyl)-1H-indole-5-carboxamide (4b), oil, NMR ($CDCl_3$) 2.65 (m, 2H), 3.05 (s, 6H), 3.25 (t, 2H), 3.70 (d. 2H), 5.00 (s, broad, 1H), 6.30 (s, broad, 1H), 7.10–7.40 (m, 4H), 7.40–7.50 (m, 3H), 8.02 (s, 1H).

EXAMPLE 5

1-(4-Fluorophenyl)-N-methyl-3-(piperidin4-yl)-1H-indole-5-carboxamide (5a) 1-(4Fluorophenyl)-N-methyl-3-(1,2,3,6-tetrahydro-4-pyridyl)-1H-indole-5-carboxamide (4a) (6.8 g) was dissolved in a mixture of acetic acid (150 mL) and trifluoroacetic acid (25 mL). $PtO_2$ (300 mg) was added and the mixture was hydrogenated at 3 ATO for 5 h at room temperature. The mixture was filtered and the solvent removed in vacuo. Water was added, pH adjusted to 10. The phases were seperated and the aqueous phase was extracted with ethyl acetate. After removal of the solvent, the product was filtered through silica gel using ethylacetatelethanol/ TEA 50:50:5 as the solvent. Evaporation of the solvents in vacuo afforded the title compound as a foam Yield 4 g. $^1$H-NMR (DMSO)1.65 (2H), 1.95 (d, 2H), 2.70 (t, 2H), 2.80 (d,3H)2.95 (t, 1H), 3.1 (d, 2H), 7.40 (t, 2H), 7.45–7,52 (m, 2H), 7.65 (m, 2H), 7.75 (d, 1H), 8.25 (s, 1H), 8.45 (q, 1H)

The following compound was prepared analogously:

N,N-Dimethyl-1-(4-fluorophenyl)-3-(piperidin-4-yl)-1H-indole-5-carboxamide (5b), foam, $^1$NMR ($CDC_3$) 1.75 (qd, 2H), 2.1 (d, 2H), 2.85 (dt, 2H), 3.00 (tt, 1H) 3.15 (s, 6H), 3.25 (t, 2H), 7.10 (s, 1H), 7.15–7.35 (m, 31, 7.35–7.50 (m, 3H), 7.80 (s, 1H)

EXAMPLE 6

5-Dimethylaminomethyl-1-(4fluorophenyl)-3-(piperidin-4-yl)-1H-indole (6a) $LiAlH_4$ (1.5 g) was slowly added to a solution of N,N-dimethyl-1-(4-fluorophenyl)-3-(piperidin-4-yl)-1H-indole-5-carboxamide (5b) (4.25 g) in THF (50 mL) keeping the temperature below 40° C. The solution was stirred 3 h at 40° C. After cooling to 0° C., water was careflilly added, the phases were separated and the aqueous phase extracted with diethylether. The organic phase was dried over $Mg_2SO_4$ and the solvent evaporated in vacuo. Yield: 3.5 g. (oil), $^1$H-NMR ($CDC_3$) 1.70 (2H), 2.05 (d, 2H), 2.25 (s, 6H), 2.85 (td, 2H), 3.00 (tt, 1H), 3.20 (d, 2H), 3.50 (s, 2H), 7.00 (s, 1H), 7.10–7.30 (m, 3H), 7.30–7.50 (m, 3H), 7.60 (s, 1H).

The following compound was prepared analogously

5-Dimethylaminomethyl-1-(4-fluorophenyl)-3-(1,2,3,6-tetrahydro-4-pyridyl)-1H-indole (6b), oil, $^1$H-NMR: 2.30 (s, 6H), 2.50 (m, 2H), 3.20 (t, 2H), 3.50 (s, 2H), 3.70 (q, 2H) 6.35 (m, 1H) 7.15–7.35 (m, 4H), 7.40–7.55 (m, 3H), 7.85 (s, 1H)

EXAMPLE 7

1-(4-Fluorophenyl)3-[1-[2-(2-imidazolidinon-1-yl)ethyl]-4-piperidinyl]-N-metiyl-1H-indole-5-carboxamide (7a)

1-(4-Fluoropheny)-N-methyl-3-(piperidin4-yl)-1H-indole-5-carboxamide (5a) (4.4 g), $K_2CO_3$ (5.2 g), KI (1 g) and 1-(2-chloroethyl)-imidazolidin-2-on (2.2 g) was refluxed for 8 h in methyl isobutyl ketone. The solution was filtered hot and the residue washed with methyl isobutyl ketone. After evaporation of the solvents, the compound was dissolved in methylene chloride and washed twice with water. The compound was purified by flash chromatography (EtOAc/MeOH/TEA 80/15/5) Yield 3.5 g. Mp.: 150–155° C. (ethanolldiethyl ether 50/50). $^1$H-NMR (DMSO) 1.75 (dq, 2H), 2.0 (d, 2H), 2.15 (t, 2H), 2.45 (t, 2H), 2.82 (d, 3H), 2.85 (t, 1H), 3.02 (d, 2H), 3.2 (q, 4H), 3.4 (q, 2H), 6.25 (s, 1H), 7.40 (t, 2H), 7.49 (m, 2H), 7.60 (m, 2H), 7.70 (d, 1H), 8.20 (s, 1H), 8.4 (q, 1H)

The following compounds were prepared analogously:

N,N-Dimethyl-1-(4-fluorophenyl)-3-[1-[2-(2-imidazolidinon-1-yl)ethyl]4-piperidinyl]-1H-indole-5-carboxamide (7b)

Mp. 172–176 (acetone). $^1$H-NMR ($CDCl_3$) 1.80 (dq, 2H), 2.05 (d, 2H), 2.15 (t, 2H), 2.55 (t, 2H), 2.90 (tt, 1H), 3.10 (m, 8H), 3.40 (m, 4H), 3.50 (m, 2H), 4.80 (s, broad, 1H), 7.10 (s, 1H), 7.15–7.40 (m, 3H), 7.35–7.50 (m, 3H), 7.80 (s, 1H). Analysis: Calc (corrected for ⅓ mol acetone): C: 67.67, H: 6.91, N: 14.10, Found: C: 67.02, H: 6.92, N: 13.82.

1-[2-[4-[5-Dimethylaminomethyl-1-(4-fluorophenyl)-1H-indol-3-yl]-1-piperidinyl ]ethyl]-2-imidazolidinon (7c)

Mp 166–174° C. (acetone). $^1$H-NMR ($CDCl_3$) 1.80 (q, 2H), 2.05 (d, 2H), 2.18 (t, 2H), 2.25 (s, 6H), 2.57 (t, 2H), 2.85 (tt, 1H), 3.08 (d, 2H), 3.40 (q, 4H), 3.45–3.55 m, 4H), 4.40 (s, 1H), 7.00 (s, 1H), 7.15 (m, 3H), 7.30–7.50 (m, 3H), 7.60 (s, 1H).

1-[2-[4-[5-Dimethylaminomethyl-1-(4-fluorophenyl)-1H-indol-3-yl]-1,2,3,6-tetrahydropyridin-1-yl]ethyl]-2-imidazolidinon (7d) Mp 146–148° C. (acetone). $^1$H-NMR ($CDCl_3$) 2.30 (s, 6H), 2.60–2.75 (m, 4H), 2.80 (d, 2H) 3.30 (d, 2H), 3.40 (q, 4H), 3.45–3.55 (m, 4H), 4.70 (s, broad, 1H), 6.30 (s, broad, 1H), 7.10–7.25 (m, 4H), 7.30–7.50 (m, 3H), 7.85 (s, 1H)

EXAMPLE 8

1-[2-[4-[1-(4-Fluorophenyl)-5-methylaminomethyl-1H-indol-3-yl]-1-piperidinyl]ethyl]-2-imidazolidinon (8)

1-(4-Fluorophenyl)-3-[1-[2-(2-imidazolidinon-1-yl)ethyl]4-piperidinyl]-N-methyl-1H-indole-5-carboxamide (7a) (2g) and LiAIH4 was refluxed in dry THF (150 mL) for 3 h. After cooling to 0° C., water (100 mL) and aqueous NaOH (1 M, 5 mL) was carefully added. The phases were separated and the aqueous phase was extracted with ethyl acetate. After removal of the solvent, the compound was purified by flash chromatography (EtOAc/MeOH/TEA 80/15/5). Yield 0.3 g (oil). $^1$H-NMR (DMSO) 1.72 (q, 2H), 1.97 (d, 2H), 2.12 (t, 2H), 2.28 (s, 3H), 2.45 (t, 2H), 2.77 (tt, 1H), 3.00 (d. 2H), 3.10–3.60 (m, 6H) 3.72 (s, 2H), 6.25 (s, 2H), 7.14 (d. 1H), 7.35–7.45 (m, 4H), 7.55–7.65 (m, 3H)

EXAMPLE 9

1-[2-[4-[5-aminomethyl-1-(4-fluorophenyl)-1H-indol-3-yl]-1-piperidinyl]ethyl]-2-imidazolidinon (9)

5-Cyano-1-(4-fluorophenyl)-3-[1-[2-(2-imidazolidinon-1-yl)ethyl]-1,2,3,6-tetrahydropyridin4-yl]-1H-indole (Perregaard, J.; Bøgesø, K. P.; Hyttel, J.; Sánches, C.: *J Med. Chem.*, 1992, 35, 1092–1101) (4.6 g) was hydrogenated with $PtO_2$ in acetic acid at 3 ATO for 5 h. Ice and ammonium hydroxide was added to pH 9 and the aqueous phase was extracted with ethyl acetate. The combined organic phases were washed with water, dried over $MgSO_4$ and the solvent was removed in vacuo. The title compound was purified by preparative HPLC (ethanol/$NH_4OH$ 100/4). Yield 0.9 g, mp. 171–175° C. (diethyl ether). $^1$H-NMR ($CDCl_3$) 1.85 (d, 2H), 2.10 (d, 2H), 2.25 (td, 2H), 2.60 (t, 2H), 2.90 (tt, 1H), 3.10 (d, 2H), 3.4 (q, 4H), 3.6 (q, 2H), 3.95 (s, 2H), 4.70 (s, broad, 1H), 7.00 (s, 1H), 7.10–7.25 (m, 3H), 7.30-7-50 (m, 3H), 7.60 (s, 1H). Analysis: Calc (corrected for 1% water): C: 68.22, H: 7.01, N: 15.92 Found: C: 67.51, H: 6.90, N: 15.37

Pharmacological Testing

As mentioned above, the compounds of the invention have selectivity for $cc_1$-adrenoceptors compared to related compounds such as sertindole. The affinity of the compounds of the invention for two receptors, namely dopamine $D_2$ and the 5-HT$_2$A receptor, for which related compounds such as sertindole have high affinity, has been determined.

The compounds of the invention have been tested using well recognised and reliable methods. The tests are as follows:

INHIBITION OF [$^3$H]-PRAZOSIN BINDING TO $\alpha_1$-ADRENOCEPTORS IN RAT BRAIN IN VITRO By this method, the inhibition by drugs of the binding of [$^3$H-prazosin (0.25 nM) to $\alpha_1$-andrenoceptors in membranes from rat brain is determined in vitro. Method and results in Hyttel & Larsen, J. Neurochem. 1985, 44, 1615–1622; Skarsfeldt & Hyttel, Eur. J. Phanmacol. 1986,125, 323–340; Hyttel & Larsen, In: Research advances in New Psychopharmacological Treatments for Alcoholism (eds. Naranjo & Sellers). Elsevier 1985, pp. 107–119.

Procedure

Male Wistar Mol:Wist) rats (125–250 g) are sacrificed and brain tissue is dissected and weighed. The tissue is homogenized (Ultra Turrax, 10 se) in 10 mL of ice cold 50 mM tris buffer pH 7.7 (at 25° C.). The homogenate is centifiged twice at 20,000 g for 10 min at 4° C. with rehomogenization of the pellet in 10 ml ice-cold buffer. The final pellet is homogenized in 250 vol (w/v) ice-cold buffer.

Incubation tubes (96 deep-well titer plate) kept on ice receive 50 mL of drug solution in water (or water for total binding) and 50 mL of [$^3$H]-prazosin (final concentration 0.25 nM). The binding experiment is initiated by addition of 1000 mL of tissue suspension (final tissue content corresponds to 3 mg original tissue) and by placing the 96 deep well titer plate in a 25° C. water bath. AU tests are made in triplicates. After incubation for 20 min, the samples are filtered on a Brandel harvester under vacuum (18 inch. Hg) through printed filtermat B (13 mm). Titerplates and filter are washed 1×10 sec flow 50 L/h with ice cold buffer.

The filter mat is dried for 1 h at 110° C. and then placed in a sample bag with Meltilex B/HS (14.5 g) and melted together on the T-Tray heat sealer. Radioactivity is determined by counting in the 1205 Beta-plate scintillation counter (Wallac).

Specific binding is obtained by subtracting nonspecific binding estimated in the presence of 1 mM of prazosin.

For determination of the inhibition of binding, five concentrations of drugs covering 3 decades are used.

The $ICs_{50}$-value is determined as the concentration at which the binding is 50% of the total binding in control samples minus the nonspecific binding in the presence of 1 mM of prazosin.

[$^3$H]-prazosin from New England Nuclear (TRK 647; 0.37–1.1 TBq/mmol).

INHIBITION OF [$^3$H]-KETANSERIN BINDING TO SEROTONIN $S_2$ (5HT$_{2A}$) RECEPTORS IN RAT CORTEX IN VITRO

By this method, the inhibition by drugs of the binding of [$^3$H]-ketanserin (0.5 nM) to serotonin $S_2$ (5-HT$_2$) receptors in membranes from rat cortex is determined in vitro. Method in Hyttel, Pharmacology & Toxicology 1987, 61, 126–129.

Procedure

Male Wistar (Mol:Wist) rats (125–250 g) are sacrificed and cortical tissue is dissected and weighed. The tissue is homogenized (Ultra Turrax, 10 sec) in 10 mL of ice cold 50 mM tris buffer pH 7.7 (at 25° C.). The centrifige glassware used in this step has been rinsed by sonication for 10 min in ethanol. The homogenate is centrifuged twice at 20,000 g for 10 min. at 4° C., with rehomogenization of the pellet in 10 mnL ice-cold buffer. The final pellet is homogenized in 250 vol (w/v) ice-cold buffer.

Incubation tubes (96 deep well titer plate) kept on ice receive 50 mL of [$^3$H]-ketanserin (final concentration 0.5 nM).

The binding experiment is initiated by addition of 1000 mL of tissue suspension (final tissue content corresponds to 4 mg original tissue) and by placing the 96 deep well titer plate in a 37° C. water bath. All tests are made in triplicates.

After incubation for 30 min, the samples are filtered on a Brandel harvester under vacuum (18 inch Hg) through printed filter mat B (13 mm). Titerplate and filter are washed 2×10 sec. flow 50L/h with ice cold buffer.

The printed filter mat with purred labelled tissue are dried for 1 h at 110° C. and hereafter placed in a sample bag with Meltilex B/HS 14.5 g and melted together on the T-tray heat seal. Radioactivity is determined by counting in the 1205 beta-plate scintillation counter (Wallac).

Specific binding is obtained by subtracting the nonspecific binding in the presence of 1 mM mianserin.

For determination of the inhibition of binding, five concentrations of drugs covering 3 decades are used.

The $IC_{50}$-value is determined as the concentration at which the binding is 50% of the total binding in control samples minus the nonspecific binding in the presence of 1 mM mianserin.

[$^3$H]-ketanserin=(ethylene-$^3$H)-ketanserin hydrochloride from New England Nuclear, specific activity 60–80 Ci/nmnol.

Inhibition of [$^3$H]-Spiperone Binding to Dopamnine $D_2$ Receptors in Rat Corpus Striatum in vitro By this method, the inhibition by drugs of the binding of [$^3$H]-spiperone (=$^3$H]-spiro-peridol) (0.5 nM) to dopamine D-2 receptors in membranes from rat corpus striatum is determined in vitro. Method and results in Hyttel, J. Acta. PharmacoL. ToxicoL. 1986, 59, 387. This is a test for dopamnine $D_2$ receptor binding affinity in vitro.

Procedure

Male Wistar (Mol:Wistar) rats (125–250 g) are sacrificed and striatal tissue is dissected and weighed. The tissue is homogenized (Ultra Turrax, 10 sec.) in 10 mL of ice-cold 50 mM K-phosphate buffer pH 7.4 (at 25° C.). The homogenate is centrifuiged twice at 20,000 g for 10 min at 4° C. with rehomogenization of the pellet in 10 mL ice-old buffer. The final pellet is homogenized in 1300 vol (w/v) ice-cold buffer.

Incubation tubes kept on ice in triplicate receive 100 µl of drug solution in water (or water for total binding) and 4000 µl of tissue suspension (final tissue content corresponds to 3.08 mg original tissue). The binding experiment is initiated by addition of 100 µl of [$^3$H]-spiperone (final concentration 0.5 nM) and by placing the tubes in a 37° C. water bath. After incubation for 10 min, the samples are filtered under vacuum (0–50 mBar) through Whatman GF/F filters (25 mm). The tubes are rinsed with 5 mL ice-old buffer which are then poured on the filters. Thereafter, the filters are washed with 2×5 mL of buffer. The filters are placed in counting vials and 4 mL of appropriate scintillation fluid (e.g. Picofluor™$_{15}$) are added. After shaking for 1 h and storage for 2 hrs in the dark, the content of radioactivity is determined by liquid scintillation counting. Specific binding is obtained by subtracting the nonspecific binding in the presence of 10 μM of 6,7-ADTN.

For determination of the inhibition of binding, five concentrations of drugs covering 3 orders of magnitude are used.

The IC$_{50}$ value is determined as the concentration at which the binding is 50% of the total binding in control samples minus the nonspecific binding in the presence of 10 μM of 6,7-ADTN

[$^3$H]-Spiperone=[phenyl-4-$^3$H]-spiperone from Amersham International plc. England, specific activity 15–25 Ci/mmol.

The results obtained are presented in table 1 below:

TABLE 1

| Compound | IC$_{50}$ values in nM | | |
|---|---|---|---|
| | α$_1$ | D$_2$ | 5-HT$_{2A}$ |
| Sertindole | 3.4 | 4.1 | 0.39 |
| Prazosin | 0.36 | 11000 | 3300 |
| 7b | 5.4 | 170 | 18 |
| 7c | 1.3 | 180 | 50 |
| 7d | 0.53 | 35 | 80 |
| 9 | 0.49 | 180 | 84 |

The IC$_{50}$ values for compounds of the present invention, a closely related compound, sertindole, and a well known a,-antagonist, prazosin, are presented in Table 1. It is very clear that the compounds of the invention have high affimty for α$_1$-adrenoceptors.

In particular, it is very clear that compared to the closely related compound, sertindole, the compounds of the invention are highly selective for the α$_1$-adrenoceptor.

Pharmaceutical Compositions

The pharmaceutical compositions of this invention or those which are manufactured in accordance with this invention may be administered by any suitable route for example orally in the form of tablets, capsules, powders, syrups, etc., or parenterally in the form of solutions for injection. For preparing such compositions, methods well known in the art may be used, and any pharmaceutically acceptable carriers, diluents, excipients, or other additives normally used in the art may be used.

Conveniently, the compounds of the invention are administered in unit dosage form containing said compounds in an amount of about 0.01 to 100 mg.

The total daily dose is usually in the range of about 0.05–500 mg, and most preferably about 0.1 to 50 mg of the active compound of the invention.

Formulation Examples

The pharmaceutical formulations of the invention may be prepared by conventional methods in the art.

For example: Tablets may be prepared by mixing the active ingredient with ordinary adjuvants and/or diluents and subsequently compressing the mixture in a conventional tabletting machine. Examples of adjuvants or diluents comprise: corn starch, potato starch, talcum, magnesium stearate, gelatine, lactose, gums, and the like. Any other adjuvants or additives usually used for such purposes such as colourings, flavourings, preservatives etc. may be used provided that they are compatible with the active ingredients. Solutions for injections may be prepared by dissolving the active ingredient and possible additives in a part of the solvent for injection, preferably sterile water, adjusting the solution to desired volume, sterilisation of the solution and filling in suitable ampules or vials. Any suitable additive conventionally used in the art may be added, such as tonicity agents, preservatives, antioxidants, etc.

Typical examples of recipes for the formulation of the invention are as follows:

1) Tablets containing 5.0 mg of a compound of the invention calculated as the free base:

| | |
|---|---|
| Compound of the invention | 5.0 mg |
| Lactose | 60 mg |
| Maize starch | 30 mg |
| Hydroxypropylcellulose | 2.4 mg |
| Microcrystalline cellulose | 19.2 mg |
| Croscarmellose Sodium Type A | 2.4 mg |
| Magnesium stearate | 0.84 mg |

2) Tablets containing 0.5 mg of a compound of the invention calculated as the free base:

| | |
|---|---|
| Compound of the invention | 0.5 mg |
| Lactose | 46.9 mg |
| Maize starch | 23.5 mg |
| Povidone | 1.8 mg |
| Microcrystalline cellulose | 14.4 mg |
| Croscarmellose Sodium Type A | 1.8 mg |
| Magnesium stearate | 0.63 mg |

3) Syrup containing per millilitre:

| | |
|---|---|
| Compound of the invention | 25 mg |
| Sorbitol | 500 mg |
| Hydroxypropylcellulose | 15 mg |
| Glycerol | 50 mg |
| Methyl-paraben | 1 mg |
| Propyl-paraben | 0.1 mg |
| Ethanol | 0.005 ml |
| Flavour | 0.05 mg |
| Saccharin sodium | 0.5 mg |
| Water | ad 1 mL |

4) Solution for injection containing per millilitre:

| | |
|---|---|
| Compound of the invention | 0.5 mg |
| Sorbitol | 5.1 mg |
| Acetic Acid | 0.05 mg |
| Saccharin sodium | 0.5 mg |
| Water | ad 1 mL |

What is claimed is:

1. A 5-aminoalkyl and 5-aminocarbonyl substituted indole compound having the formula

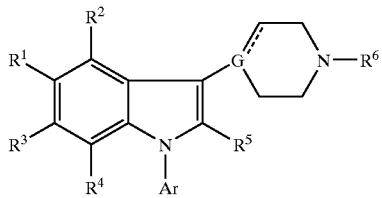

I wherein
R$^1$ is —(CH$_2$)$_{n-1}$-CONR$^{10}$R$^{11}$, —(CH$_2$)$_n$-NR$^{10}$R$^{11}$ or

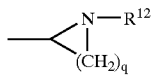

wherein R$^{10}$ and R$^{11}$ are independently selected from hydrogen, C$_{1-6}$-alkyl, C$_{2-6}$-alkenyl, C$_{2-6}$-alkenyl, C$_{3-8}$-alkynyl, C$_{3-8}$-cycloalkyl, C$_{3-8}$-cycloalkyl-C$_{1-6}$-alkyl, aryl-C$_{1-6}$-alkyl, aryl, acyl, amino-C$_{1-6}$-alkyl and mono- or di-C$_{1-6}$-alkylamino-C$_{1-6}$-alkyl, R$^{12}$ is hydrogen, or C$_{1-6}$-alkyl, n is 1 to 3 and q is 2 to 5;

G is C, or CH; the dotted line meaning a bond when G is C, and the dotted line meaning no bond when G is CH, N;

Ar is phenyl optionally substituted with one or more substituents independently selected from halogen, C$_{1-6}$-alkyl, C$_{1-6}$-alkoxy, hydroxy, trifluoromethyl and cyano, or Ar is 2-thienyl, 3-thienyl, 2-furanyl, 3-furanyl, 2-thiazolyl, 2-oxazolyl, 2-imidazolyl, 2-pyridyl, 3-pyridyl, or 4-pyridyl;

R$^2$, R$^3$, R$^4$ and R$^5$ are independently selected from hydrogen, C$_{1-6}$-alkyl, C$_{1-6}$-alkoxy, hydroxy, halogen, trifluoromethyl, nitro, cyano, amino, C$_{1-6}$-alkylamino and C$_{1-6}$-dialkylamino;

R$^6$ is hydrogen, or C$_{3-8}$-cycloalkyl, C$_{3-8}$-cycloalkyl-C$_{1-6}$-alkyl, C$_{2-6}$-alkenyl or C$_{2-6}$-alkenyl, which may optionally be substituted with one or two hydroxy groups, any hydroxy group present being optionally esterified with an aliphatic carboxylic acid having from two to twenty-four carbon atoms inclusive, or R$^6$ is a group of the Formula II or III:

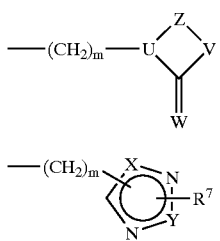

wherein m is an integer from 2–6;

W is O or S;
U is N or CH;
Z is —(CH$_2$)$_p$, p being 2 or 3, or Z is —CH=CH— or 1,2-phenylene optionally substituted with halogen or trifluoromethyl, or Z is —COCH$_2$- or —CSCH$_2$-;
V is O, S, CH$_2$, or NR$^9$, wherein R$^9$ is hydrogen, or C$_{1-6}$-alkyl, C$_{2-6}$-alkenyl or C$_{2-6}$-alkenyl, which may optionally be substituted with one or two hydroxy groups, or a C$_{3-8}$-cycloalkyl or C$_{3-8}$-cycloalkyl-C$_{1-6}$-alkyl group; X is N, C, or CH; Y is N, C, or CH; provided at least one of X and Y s N; and R$^7$ is hydrogen, or
C$_{1-6}$-alkyl;

or a pharmaceutically acceptable acid addition salt thereof.

2. A compound according to claim 1, wherein R$^1$ is —CONR$^{10}$R$^{11}$ or —(CH$_2$)$_n$-NR$^{10}$R$^{11}$ wherein R$^{10}$ and R$^{11}$ are independently selected from hydrogen and C$_{1-6}$ alkyl.

3. A compound according to claim 1, wherein R$^6$ is a group of formula II.

4. A compound according to claim 1, which is selected from 1-(4-Fluorophenyl)-3-[1-[2-(2-imidazolidinon-1-yl)ethyl]-4-piperidinyl]-N-methyl-1H-indole-5-carboxamide;

N,N-Dimethyl-1-(4-fluorophenyl)-3-[1-[2-(2-imidazolidinon-1-yl)ethyl]-4-piperidinyl ]-N-1H-indole-5-carboxamide;

1-[2-[4-[5-Dimethylaminomethyl-1-(4-fluorophenyl)-1H-indol-3-yl]-1-piperidinyl]ethyl]-2-imidazolidinon;

1-[2-[4-[5-Dimethylaminomethyl-1-(4-fluorophenyl)-1H-indol-3-yl]-1,2,3,6-tetrahydropyridin-1-yl]ethyl]-2-imidazolidinon;

1-[2-[4-[1-(4-fluorophenyl)-5-methylaminomethyl-1H-indol-3-yl]-1piperidinyl ]ethyl]-2-imidazolidinon; or 1-[2-[4-[5-aminomethyl-1-(4-fluorophenyl)-1H-indol-3-yl]-1-piperidinyl]ethyl]-2-imidazolidinon; or a pharmaceutically acceptable acid addition salt thereof.

5. A compound according to any one of claims 1 to 4 wherein one of the elements has an effective amount of [$^{11}$C]-methyl for radio-imaging.

6. A compound according to claim 5 wherein the compound is radiolabeled with an effective amount of [$^{11}$C]-methyl for radio-imaging.

7. A pharmaceutical composition comprising a therapeutically effective amount of:
at least one compound according to claim 1 or a pharmaceutically acceptable acid addition salt thereof in combination with one or more pharmaceutically acceptable carriers or diluents.

8. A method for the treatment of a disorder or disease responsive to antagonism of $\alpha_1$-adrenoceptors in a mammal comprising administering a compound according to claim 1 or an acid addition salt thereof to said mammal.

9. A method for the treatment of psychosis in a mammal comprising administering a compound according to claim 1 or an acid addition salt thereof to said mammal.

* * * * *